US008772525B2

(12) United States Patent
Katsoulis et al.

(10) Patent No.: US 8,772,525 B2
(45) Date of Patent: Jul. 8, 2014

(54) METHOD FOR PREPARING A DIORGANODIHALOSILANE

(75) Inventors: Dimitris Katsoulis, Midland, MI (US); Robert Larsen, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 13/639,518

(22) PCT Filed: Mar. 31, 2011

(86) PCT No.: PCT/US2011/030683
§ 371 (c)(1),
(2), (4) Date: Oct. 5, 2012

(87) PCT Pub. No.: WO2011/149588
PCT Pub. Date: Dec. 1, 2011

(65) Prior Publication Data
US 2013/0066096 A1 Mar. 14, 2013

Related U.S. Application Data

(60) Provisional application No. 61/349,242, filed on May 28, 2010.

(51) Int. Cl.
C07F 7/18 (2006.01)
(52) U.S. Cl.
USPC ............................ 556/478; 556/472; 556/473
(58) Field of Classification Search
CPC ..................................... C07F 7/16; C07F 7/14
USPC ......................................... 556/478, 472, 473
See application file for complete search history.

(56) References Cited

U.S. PATENT DOCUMENTS

| 2,403,370 | A | | 7/1946 | Hurd |
| 2,888,476 | A | | 5/1959 | Little et al. |
| 3,057,686 | A | | 10/1962 | Muetterties |
| 4,314,908 | A | * | 2/1982 | Downing et al. ............. 502/244 |
| 4,526,769 | A | | 7/1985 | Ingle et al. |
| 4,836,997 | A | | 6/1989 | Lepage et al. |
| 4,888,435 | A | | 12/1989 | Chadwick et al. |
| 4,946,980 | A | | 8/1990 | Halm et al. |
| 4,973,725 | A | * | 11/1990 | Lewis et al. .................... 556/472 |
| 6,156,380 | A | | 12/2000 | Aramata et al. |
| 6,790,749 | B2 | | 9/2004 | Takemura et al. |
| 6,887,448 | B2 | | 5/2005 | Block et al. |
| 7,223,879 | B2 | | 5/2007 | Buchwald et al. |
| 7,442,824 | B2 | | 10/2008 | Paetzold et al. |
| 7,559,969 | B2 | | 7/2009 | Sanjurjo et al. |
| 7,716,590 | B1 | | 5/2010 | Nathan |
| 8,124,809 | B2 | | 2/2012 | Masaoka et al. |
| 2005/0074387 | A1 | | 4/2005 | Bulan et al. |
| 2005/0220514 | A1 | | 10/2005 | Hisakuni |
| 2006/0165580 | A1 | * | 7/2006 | Lipshutz ........................ 423/314 |
| 2010/0280295 | A1 | | 11/2010 | Armbruester et al. |

FOREIGN PATENT DOCUMENTS

| CA | 2829701 A2 | 9/2012 |
| DE | 3024319 | 1/1982 |
| DE | 4041644 A1 | 6/1992 |
| DE | 19654154 | 6/1997 |
| JP | 51-23226 | 2/1976 |
| JP | 2009111202 | 5/2009 |
| WO | 0248034 | 6/2002 |
| WO | 2005051963 | 6/2005 |
| WO | 2009037301 | 3/2009 |

OTHER PUBLICATIONS

Dallas T. Hurd, The Vapor Phase Alkylation and Hydrogenation of Chlorosilanes, J. Am. Chem. Soc., 1945, 67 (9), pp. 1545-1548.
Eaborn, C. et al., Further studies on reactions of organic halides with disilanes catalysed by transition metal complexes, Journal of Organometallic Chemistry, vol. 225, 1982, pp. 331-341.
Golubtsov, S.A. et al., Role of the Products of Partial Chlorination of Silicon in the Formation of Methyltrichlorosilane, Russian Chemical Bulletin, vol. 21, No. 3 (1975), pp. 584-586.
H. Walter, Mechanism of the silicide-catalysed hydrodehalogenation of silicon tetrachloride to trichlorosilane, J. Chem. Soc., Faraday Trans., 1996,92, 4605-4608.
Juszczyk et al., of Pd/SiO2 catalysts during high temperature reduction., Department of Catalysis on Metals, Institute of Physical Chemistry, Polish Academy of Sciences, Warsaw, Pol. Catalysis Letters (2002), 78 (1-4), 95-98.
Juszczyk et al., Transformation of Pd/SiO2 into palladium silicide during reduction at 450° and 500° C., Institute of Physical Chemistry, Department of Catalysis on Metals, Polish Academy of Sciences, Warsaw, Pol. Journal of Catalysis (2003), 220(2), 299-308.
Lobusevich, N.P. et al., Reactions During Direct Synthesis of Alkylchlorosilanes., vol. 48, No. 11, 1978, pp. 2534-2541. (Abstract).
Moreno-Manas, Marcial et al., Formation of Carbon-Carbon Bonds under Catalysis by Transition-Metal Nanoparticles, Department of Chemistry, Universitat Autonoma de Barcelona, Barcelona, Spain. Accounts of Chemical Research (2003), 36(8), 638-643.

(Continued)

Primary Examiner — Sudhakar Katakam
Assistant Examiner — Pancham Bakshi
(74) Attorney, Agent, or Firm — Matthew T. Fewkes; Catherine U. Brown

(57) ABSTRACT

A method of preparing a diorganodihalosilane comprising the separate and consecutive steps of (i) contacting a copper catalyst with a mixture comprising hydrogen gas and a silicon tetrahalide at a temperature of from 500 to 1400° C. to form a silicon-containing copper catalyst comprising at least 0.1% (w/w) of silicon, wherein the copper catalyst is selected from copper and a mixture comprising copper and at least one element selected from gold, magnesium, calcium, cesium, tin, and sulfur; and (ii) contacting the silicon-containing copper catalyst with an organohalide at a temperature of from 100 to 600° C. to form at least one diorganodihalosilane.

19 Claims, No Drawings

(56) References Cited

OTHER PUBLICATIONS

Beccalli, Egle M., et al., C-C, C-O, C-N. Bond Formation on sp2 Carbon by Palladium(II)-Catalyzed Reactions Involving Oxidant Agents., Istituto di Chimica Organica A. Marchesini, Facolta di Farmacia, Universita di Milano, Milan, Italy. Chemical Reviews (Washington, DC, United States) (2007), 107(11), 5318-5365.

Methivier, et al., Pd/SiC catalysts. Characterization and catalytic activity for the methane total oxidation.. Institut de Recherches sur la Catalyse-CNRS, conventionne a l'Universite Claude Bernard Lyon 1, Villeurbanne, Fr. Journal of Catalysis (1998), 173(2), 374-382.

Srebowata, A. et al., Hydrodechlorination of 1,2-dichloroethane over differently reduced Pd/SiO2 catalysts., Institute of Physical Chemistry, Polish Academy of Sciences, Warsaw, Pol. Polish Journal of Chemistry (2003), 77(12), 1841-1848.

Tanaka, Miyoko et al., Nanomaterials Laboratory, National Institute for Materials Science, Tsukuba, Sakura, Japan. Journal of Crystal Growth (2002), 237-239(Pt. 1), 254-258.

Terao, Jun et al., Transition metal-catalyzed C-C bond formation reactions using alkyl halides., Department of Applied Chemistry and Center for Atomic and Molecular Technologies, Graduate School of Engineering, Osaka University, 2-1 Yamadaoka, Suita, Osaka, Japan. Bulletin of the Chemical Society of Japan (2006), 79(5), 663-672.

Vijh, A. K. et al., Discovery of some new stable electrocatalytic materials for the anodic oxidation of hydrazine., Inst. Rech. Hydro-Quebec, Varennes, QC, Can. Journal of Materials Science Letters (1993), 12(2), 113-15.

Vijh, A. K. et al., Electrochemical activity of silicides of some transition metals for the hydrogen evolution reaction in acidic solutions., International Journal of Hydrogen Energy (1990), 15(11), 789-94.

Yin, Lunxiang, et al., Carbon-carbon coupling reactions catalyzed by heterogeneous palladium catalysts., Institute fuer Chemie, Humboldt-Universitaet Berlin, Berlin, Germany. Chemical Reviews (Washington, DC, United States) (2007), 107(1), 133-173.

Mulla, et. al., "Reaction of Magnesium Silicide & Silicon Tetrachloride/Trichlorosilane in Presence of Hydrogen", Indian Journal of Chemistry, Sep. 1988, pp. 756-758, vol. 27A.

* cited by examiner

METHOD FOR PREPARING A DIORGANODIHALOSILANE

CROSS REFERENCE TO RELATED APPLICATIONS

This application is a U.S. national stage filing under 35 U.S.C. §371 of PCT Application No. PCT/US11/30683 filed on Mar. 31, 2011, currently pending, which claims the benefit of U.S. Provisional Patent Application No. 61/349,242 filed May 28, 2010 under 35 U.S.C. §119 (e). PCT Application No. PCT/US11/30683, and U.S. Provisional Patent Application No. 61/349,242 are hereby incorporated by reference.

FIELD OF THE INVENTION

The present invention relates to a method of preparing a diorganodihalosilane comprising the separate and consecutive steps of (i) contacting a copper catalyst with hydrogen and a silicon tetrahalide to form a silicon-containing copper catalyst, and (ii) contacting the silicon-containing copper catalyst with an organohalide to form a diorganodihalosilane.

BACKGROUND OF THE INVENTION

Diorganodihalosilanes are hydrolyzed to produce a wide range of polyorganosiloxanes, which are sold into many different industries. Typically, diorganodihalosilanes are produced commercially by the Mueller-Rochow Direct Process, which comprises passing an organohalide, such as methyl chloride, over zero-valent silicon in the presence of a copper catalyst and various promoters to produce a mixture of organohalosilanes. Of the organhalosilanes produced in the Direct Process, dimethyldichlorosilane is the most valuable.

A typical commercial process to make zero-valent silicon comprises the carbothermic reduction of $SiO_2$ in an electric arc furnace at extremely high temperatures. Generation of these extreme temperatures requires significant amounts of energy, which adds significant cost to the process of producing zero-valent silicon. Consequently, the use of zero-valent silicon also adds significant costs to the production of diorganodihalosilanes.

In addition to the Direct Process, diorganodihalosilanes have been produced by the alkylation of silicon tetrachloride and various methylchlorosilanes by passing the vapors of these chlorosilanes together with an alkyl halide over finely divided aluminum or zinc at elevated temperatures. However, this process results in the production of a large amount of aluminum chloride or zinc chloride, which is costly to dispose of on a commercial scale.

Therefore, there is a need for a more economical method of producing diorganodihalosilanes that avoids the need for zero-valent silicon produced by reducing $SiO_2$ at extremely high temperatures and that does not require the costly disposal of byproducts.

BRIEF SUMMARY OF THE INVENTION

The present invention is directed to a method of preparing a diorganodihalosilane comprising the separate and consecutive steps of (i) contacting a copper catalyst with a mixture comprising hydrogen gas and a silicon tetrahalide at a temperature of from 500 to 1400° C. to form a silicon-containing copper catalyst comprising at least 0.1% (w/w) of silicon, wherein the copper catalyst is selected from copper and a mixture comprising copper and at least one element selected from gold, magnesium, calcium, cesium, tin, and sulfur; and (ii) contacting the silicon-containing copper catalyst with an organohalide at a temperature of from 100 to 600° C. to form at least one diorganodihalosilane.

The method of the present invention produces a diorganodihalosilane from silicon tetrahalide. Since silicon tetrahalide is a byproduct of industrial processes or may be produced using less energy than required to produce zero-valent silicon, the method of the invention may be more economical than prior processes for producing diorgandihalosilanes. Furthermore, the method does not produce large amounts of metal halide byproducts requiring costly disposal. Finally, the method produces the more valuable diorganodihalosilane with good selectivity compared to the other organosilanes produced.

The diorganodihalosilane produced by the method of the invention can be hydrolyzed in known processes to produce polyorganosiloxanes. The polyorganosiloxanes thus produced find use in many industries and applications.

DETAILED DESCRIPTION OF THE INVENTION

A method of preparing a diorganodihalosilane, the method comprising the following separate and consecutive steps:

(i) contacting a copper catalyst with a mixture comprising hydrogen gas and a silicon tetrahalide at a temperature of from 500 to 1400° C. to form a silicon-containing copper catalyst comprising at least 0.1% (w/w) of silicon, wherein the copper catalyst is selected from copper and a mixture comprising copper and at least one element selected from gold, magnesium, calcium, cesium, tin, and sulfur; and (ii) contacting the silicon-containing copper catalyst with an organohalide at a temperature of from 100 to 600° C. to form at least one diorganodihalosilane.

In step (i), a copper catalyst is contacted with a mixture comprising hydrogen gas and a silicon tetrahalide at a temperature of from 500 to 1400° C. to form a silicon-containing copper catalyst comprising at least 0.1% (w/w) of silicon. The copper catalyst is selected from copper and a mixture comprising copper and at least one element selected from gold, magnesium, calcium, cesium, tin, and sulfur.

The copper catalyst is selected from copper and a mixture comprising copper and at least one element selected from gold, magnesium, calcium, cesium, tin, and sulfur. The mixture typically comprises from 0.1 to less than 100% (w/w), alternatively from 50 to less than 100% (w/w), alternatively, from 70 to less than 100% (w/w), alternatively, from 80 to 99.9% (w/w), of copper, based on the total weight of the mixture, with the balance of the mixture being at least one of the elements described above.

The catalyst can be a supported or unsupported catalyst. Examples of supports include, but are not limited to, oxides of aluminum, titanium, zirconium, and silicon; activated carbon; carbon nanotubes; fullerenes; and other allotropic forms of carbon. In one embodiment, the support is activated carbon.

When the catalyst comprises a support, the catalyst typically comprises from 0.1 to less than 100% (w/w), alternatively from 0.1 to 50% (w/w), alternatively from 0.1 to 35% (w/w), of copper or the mixture, based on the combined weight of the support and copper or the mixture.

The catalyst can have a variety of physical forms including, but not limited to, lumps, granules, flakes, and powder.

Examples of the unsupported copper catalyst include, but are not limited to, metallic copper; mixtures of metallic copper and gold; mixtures of metallic copper, metallic gold and magnesium chloride; mixtures of metallic copper, metallic gold and sulfur; mixtures of metallic copper and tin; mixtures of metallic copper and cesium; and mixtures of metallic copper and calcium chloride. As used herein, "metallic" means that the metal has an oxidation number of zero.

Examples of the supported copper catalyst include the unsupported copper catalysts described above on an activated carbon support, where the supported copper catalyst comprises from 0.1 to 35% (w/w), of copper or the mixture, based on the weight of the support and copper or the mixture.

The unsupported and supported copper catalysts can be made by processes known in the art. For example, to make the unsupported catalyst, copper, gold, magnesium chloride, tin, and calcium may be mixed to form the copper catalysts. In addition, metal salts, including, but not limited to, halide, acetate, nitrate, and carboxylate salts, may be mixed in desired proportions and then subjected to known reduction processes. One such reduction process is described below for making the supported copper catalysts. This process may leave some salts, such as magnesium chloride, unreduced, while reducing others.

The supported copper catalyst may be prepared by, for example, making a mixture of a copper salt, such as cupric chloride, in a solvent, such as water or acid, applying the mixture to a support, and reducing the copper salt on the surface of the support. For example, $CuCl_2$ can be dissolved in water or hydrochloric acid and mixed with activated carbon. Excess $CuCl_2$ solution can then be removed, and the activated carbon-$CuCl_2$ mixture dried. The $CuCl_2$ can then be reduced on the activated carbon with hydrogen at 500° C. to give the supported copper catalyst. One skilled in the art would understand that the order of addition, reduction and multistep addition of salts and subsequent reduction can also be carried out to prepare the supported catalyst. A method of making the supported metallic catalysts is also described in detail in the examples section below. Some of these catalysts are also available commercially.

The silicon tetrahalide has the formula $SiX_4$, where X is chloro, bromo, fluoro, or iodo, alternatively chloro, bromo, or iodo, alternatively chloro.

Examples of the silicon tetrahalide include, but are not limited to, silicon tetrachloride, silicon tetrabromide, silicon tetraiodide, silicon tetrafluoride.

The reactor for (i) can be any reactor suitable for the combining of gases and solids. For example, the reactor configuration can be a packed bed, stirred bed, vibrating bed, moving bed, re-circulating beds, or a fluidized bed. When using re-circulating beds, the silicon-containing copper catalyst can be circulated from a bed for conducting (i) to a bed for conducting (ii). To facilitate reaction, the reactor should have means to control the temperature of the reaction zone.

The temperature at which the hydrogen and the silicon tetrahalide are contacted with the copper catalyst is typically from 500 to 1400° C.; alternatively from 600 to 1200° C.; alternatively from 650 to 1100° C.

The pressure at which the hydrogen and the silicon tetrahalide are contacted with the copper catalyst can be sub-atmospheric, atmospheric, or super-atmospheric. For example, the pressure is typically from 100 to 2000 kilopascals gauge (kPag); alternatively from 100 to 1000 kPag; alternatively from 100 to 800 kPag, at a temperature from 500 to 1400° C.

The mole ratio of hydrogen to silicon tetrahalide contacted with the copper catalyst is from 10,000:1 to 0.01:1, alternatively from 100:1 to 1:1, alternatively from 20:1 to 2:1, alternatively from 20:1 to 5:1.

The residence time for the hydrogen and silicon tetrahalide is sufficient for the hydrogen and silicon tetrahalide to contact the copper catalyst and form the silicon-containing copper catalyst. For example, a sufficient residence time for the hydrogen and silicon tetrahalide is typically at least 0.01 seconds (s); alternatively at least 0.1 s; alternatively from 0.1 s to 10 min; alternatively from 0.1 s to 1 min; alternatively from 0.5 s to 10 s. As used herein, "residence time" means the time for one reactor volume of reactant gases (i.e., hydrogen and silicon tetrahalide or organohalide) to pass through a reactor charged with copper catalyst. The desired residence time may be achieved by adjusting the flow rate of the hydrogen and silicon tetrahalide.

The hydrogen and silicon tetrahalide are typically fed to the reactor simultaneously; however, other methods of combining, such as by separate pulses, are also envisioned.

The copper catalyst is in a sufficient amount. As used herein, a "sufficient amount" of copper catalyst is enough catalyst to form the silicon-containing copper catalyst, described below, when the hydrogen and silicon tetrahalide are contacted with the copper catalysts. For example, a sufficient amount of catalyst is at least 0.01 mg catalyst/$cm^3$ of reactor volume; alternatively at least 0.5 mg catalyst/$cm^3$ of reactor volume; alternatively from 1 to 10,000 mg catalyst/$cm^3$ of reactor volume.

There is no upper limit on the time for which step (i) is conducted. For example, step (i) is usually conducted for at least 0.1 seconds, alternatively from 1 second to 5 hours, alternatively from 1 minute to 1 hour.

In step (ii) of the method, the silicon-containing copper catalyst is contacted with an organohalide at a temperature of from 100 to 600° C. to form at least one diorganodihalosilane.

The silicon-containing copper catalyst comprises at least 0.1% (w/w), alternatively from 0.1 to 90% (w/w), alternatively 1 to 20% (w/w), alternatively from 1 to 5% (w/w), based on the total weight of silicon-containing copper catalyst including any support, of silicon. The percentage of silicon in the silicon-containing copper catalyst can be determined using standard analytical tests. For example, the percentage of silicon may be determined using inductively coupled plasma atomic emission spectroscopy (ICP-AES) and ICP mass spectrometry (ICP-MS).

The organohalide has the formula RX, wherein R is $C_1$-$C_{10}$ alkyl or $C_4$-$C_{10}$ cycloalkyl, and X is as defined above for the silicon tetrahalide and may be the same or different as the silicon tetrahalide.

The alkyl groups represented by R typically have from 1 to 10 carbon atoms, alternatively from 1 to 6 carbon atoms, alternatively from 1 to 4 carbon atoms. The cycloalkyl groups represented by R typically have from 4 to 10 carbon atoms; alternatively 6 to 8 carbon atoms. Alkyl groups containing at least three carbon atoms can have a branched or unbranched structure. Examples of alkyl groups include, but are not limited to, methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, and decyl. Examples of cycloalkyl groups include, but are not limited to, cyclobutyl, cyclopentyl, cyclohexyl, and methylcyclohexyl.

Examples of the organohalide include, but are not limited to, methyl chloride, methyl bromide, methyl iodide, ethyl chloride, ethyl bromide, ethyl iodide, cyclobutyl chloride, cyclobutyl bromide, cyclohexyl chloride, and cyclohexyl bromide.

The reactors suitable for use in (ii) are as described for (i). The same reactor may be used for step (i) as used in step (ii); however, separate reactors may also be used.

The organohalide is typically contacted with the silicon-containing copper catalyst by feeding the organohalide into a reactor containing the silicon-containing copper catalyst produced in step (i).

The residence time of the organohalide is sufficient for the organohalide to react with the silicon-containing copper catalyst to form a diorganodihalosilane. For example, a sufficient residence time of the organohalide is typically at least 0.01 s, alternatively at least 0.1 s, alternatively from 0.5 s to 10 min, alternatively from 1 s to 1 min, alternatively from 1 to 10 s. The desired residence time can be achieved by adjusting the flow rate of the organohalide.

The temperature at which organohalide is contacted with the silicon-containing copper catalyst is typically from 100 to 600° C.; alternatively from 200 to 500° C.; alternatively from 250 to 375° C.

Step (ii) is typically conducted until the silicon in the silicon-containing copper catalyst falls below predetermined limits. For example, step (ii) is typically conducted until the silicon in the silicon-containing copper catalyst is below 90% (w/w), alternatively from 1 to 90% (w/w), alternatively from 1 to 40% (w/w), of its initial weight percent, based on the total weight of catalyst including any support. As used herein, the "initial weight percent of silicon in the silicon-containing copper catalyst" means the weight percent of silicon in the silicon-containing copper catalyst before the silicon-containing copper catalyst is contacted with the organohalide in (ii). The amount of silicon in the silicon-containing copper catalyst can be monitored by correlating diorganodihalosilane production with the weight percent of silicon in the silicon-containing copper catalyst and then monitoring diorganodihalosilane production or may be determined as described above for the silicon-containing copper catalyst.

The pressure at which the organohalide is contacted with the silicon-containing copper catalyst in (ii) can be sub-atmospheric, atmospheric, or super-atmospheric. For example, the pressure is typically from 100 to 2000 kilopascals gauge (kPag); alternatively from 100 to 1000 kPag; alternatively from 100 to 800 kPag.

The silicon-containing copper catalyst is in a sufficient amount. As used herein, a "sufficient amount" of silicon-containing copper catalyst is enough catalyst to form the diorganodihalosilane, described below, when contacted with the organohalide. For example, a sufficient amount of silicon-containing copper catalyst is at least 0.01 mg catalyst/cm$^3$ of reactor volume; alternatively at least 0.5 mg catalyst/cm$^3$ of reactor volume; alternatively from 1 to 10000 mg catalyst/cm$^3$ of reactor volume.

Step (i) and step (ii) of the method are conducted separately and consecutively. As used herein, "separately" means that the step (i) and step (ii) do not overlap or coincide. As used herein, "consecutively" means that step (ii) is performed after step (i) in the method; however, additional steps may be performed between step (i) and (ii), such as described below.

The method of the invention may also comprise purging prior to the contacting of the silicon-containing copper catalyst with the organohalide in step (ii) and prior to the contacting of the reformed silicon-containing catalyst with the organohalide in (iv). As used herein, "purging" means to introduce a gas stream to the reactor containing the silicon-containing copper catalyst to remove unwanted materials. Unwanted materials are, for example, $H_2$, $O_2$, and $H_2O$. Purging may be accomplished with an inert gas, such as argon, or with a reactive gas, such as silicon tetrachloride, which reacts with moisture thereby removing it.

In one embodiment of the invention, the silicon-containing copper catalyst and the organohalide contacted in (ii) are contacted in the absence of hydrogen, silicon tetrahalide, or both hydrogen and silicon tetrahalide.

In one embodiment, the method further comprises (iii) contacting the silicon-containing copper catalyst contacted with the organohalide in (ii) with the mixture comprising hydrogen gas and a silicon tetrahalide at a temperature of from 500 to 1400° C. to reform the silicon-containing copper catalyst comprising at least 0.1% (w/w) silicon; and (iv) contacting the reformed silicon-containing copper catalyst with the organohalide at a temperature of from 100 to 600° C. to form at least one diorganodihalosilane.

In another embodiment, the method of the invention further comprises repeating steps (iii) and (iv) at least 1 time, alternatively from 1 to $10^5$ times, alternatively from 1 to 1000 times, alternatively from 1 to 100 times, alternatively from 1 to 10 times.

If the organohalide or silicon tetrahalide are liquids at or below standard temperature and pressure, the method may further comprise pre-heating and gasifying the organohalide or silicon tetrahalide by known methods prior to contacting the silicon tetrahalide with the copper catalyst in (i) and (iii) or contacting the organohalide with the silicon-containing copper catalysts in (ii) and (iv). Alternatively, the process may further comprise bubbling the hydrogen through liquid silicon tetrahalide to vaporize the silicon tetrahalide prior to contacting with the copper catalysts in step (i) and the silicon-containing copper catalyst in (iii).

The process may further comprise recovering the diorganodihalosilane produced. The diorganodihalosilane may be recovered by, for example, removing gaseous diorganodihalosilane from the reactor followed by isolation by distillation.

The diorganodihalosilane produced by the process described and exemplified above has the formula $R_2SiX_2$, wherein R and X are as defined and exemplified above for the organohalide.

Examples of diorganodihalosilanes prepared according to the present process include, but are not limited to, dimethyldichlorosilane (i.e., $(CH_3)_2SiCl_2$), dimethyldibromosilane, dimethyldiiodosilane, dimethyldifluorosilane, diethyldichlorosilane, diethyldibromosilane, diethyldiiodosilane, dicyclohexyldichlorosilane, and dicyclohexyldibromosilane.

The process may also produce other organohalosilanes, such as those having the formula $R_aHSiX_{3-a}$, $RSiX_3$, and $R_3SiX$, where R and X are as defined above and a is 1 or 2. The process may also produce hydrohalosilanes, such as those having the formula $HSiX_3$, where X is as defined above.

The method of the present invention produces diorganodihalosilanes from silicon tetrahalide. Since silicon tetrahalide is a byproduct of other industrial processes and may be produced using less energy than required to produce zero-valent silicon, the method of the invention may be more economical than methods of producing diorganodihalosilanes using zero-valent silicon. Furthermore, the method does not produce large amounts of metal halide byproducts requiring costly disposal. Still further, the method produces the more valuable diorganodihalosilanes with good selectivity compared to other organosilanes. Finally, the copper catalyst may be reformed and reused in the method, and the reforming and reuse provides increasing diorganodihalosilane production and selectivity.

The process of the present invention produces diorganodihalosilanes that can be hydrolyzed in known processes for producing polyorganosiloxanes. The polyorganosiloxanes thus produced find use in many industries and applications.

EXAMPLES

The following examples are presented to better illustrate the method of the present invention, but are not to be considered as limiting the invention, which is delineated in the appended claims. Unless otherwise noted, all parts and percentages reported in the examples are by weight. The following table describes the abbreviations and terms used in the examples:

TABLE 1

List of abbreviations and terms used in the examples.

| Abbreviation | Word |
|---|---|
| g | gram |
| mg | milligram |
| Me | methyl |
| wt | weight |
| % | percent |
| mol | mole |
| hr | hour |
| °C. | degrees Celsius |
| NA | Not Applicable |
| mL | milliliters |
| cm | centimeter |
| sccm | standard cubic centimeters per minute |
| TCD | thermal conductivity detector |
| Sel. | selectivity |
| $Me_2SiCl_2$ Selectivity | weight of dimethyldichlorosilane divided by the sum of the weights all other volatile Si containing products |
| $Me_2SiCl_2$ wt. % | weight percent of $Me_2SiCl_2$ leaving the reactor based upon the total mass leaving the reactor |
| GC | gas chromatograph |

Method of Producing Copper Catalyst Comprising Copper, Gold, and Magnesium $CuCl_2.2H_2O$ (99+%, 1.0526 g), 0.0192 g $AuCl_3$ (99%), and 0.0357 g $MgCl_2.6H_2O$ (99.995%) were dissolved in 2.1 mL of deionized $H_2O$ and 0.1 mL concentrated HCl to form a metal salt mixture. This metal salt mixture was then added to 1.1734 g of activated carbon. Excess liquid not absorbed by the activated carbon was dabbed away, and then the activated carbon was dried at 175° C. The dried activated carbon had a final dry weight of 1.9355 g. Based on the starting weight of the activated carbon and metal solution loading, the metal loading on the activated carbon was calculated to be 22.3% (w/w) Cu, 0.71% (w/w) Au, and 0.24% (w/w) Mg. The metal loaded activated carbon (0.77 g) was charged into a quartz glass tube and placed into a flow reactor. Activation and reduction of the catalyst was performed by flowing $H_2$ at 100 sccm (controlled via Omega FMA 5500 mass flow controller) into the glass tube containing the catalyst in the reactor at 600° C. for 2 hours. The heating was accomplished using a Lindberg/Blue Minimite 1 inch tube furnace.

Reaction Apparatus

The reaction apparatus comprised a 4.8 mm inner diameter quartz glass tube in a flow reactor. The reactor tube was heated using a Lindberg/Blue Minimite 2.54 cm tube furnace. Omega FMA 5500 mass flow controllers were used to control gas flow rates. A stainless steel $SiCl_4$ bubbler was used to introduce $SiCl_4$ into the $H_2$ gas stream. The amount of $SiCl_4$ in the $H_2$ gas stream was adjusted by changing the temperature of the $SiCl_4$ in the bubbler according to calculations using well-known thermodynamic principles. The reactor effluent passed through an actuated 6-way valve from Vici.

Reagents

The activated carbon, $CuCl_2.2H_2O$, $AuCl_3$, and $MgCl_2.6H_2O$ and other reagents used in the examples were purchased from Sigma Aldrich, Miwaukee, Wis.

Product Analysis

The effluent of the reactor containing the products and byproducts was passed through an actuated 6-way valve (Vici) with constant 100 uL injection loop before being discarded. Samples were taken from the reaction stream by actuating the injection valve and the 100 uL sample passed directly into the injection port of a 7890A Agilent GC-MS for analysis with a split ratio at the injection port of 100:1. The GC contained two 30 m SPB-Octyl columns (Supelco, 250 um inner diameter, 0.25 um thick film), which were placed in parallel such that the sample was split evenly between the two columns. One column went to a TCD for quantization of the reaction products and the other column went to a mass spectrometer (Agilent 7895C MSD) for sensitive detection of trace products and positive identification of any products that formed. The columns were heated by an Agilent LTM module (i.e., the columns were wrapped with heating elements and thermocouples such that they were precisely and rapidly ramped to the desired temperature).

Flow Rates

Flow rate ratios were determined using known thermodynamic principles with the flow rates, at standard temperature and pressure, of hydrogen, $SiCl_4$, and methyl chloride.

Example 1

Copper catalyst (0.77 g) comprising an activated carbon supported mixture of copper, gold, and magnesium, prepared as described above, was treated in $H_2/SiCl_4$ for 30 min at 750° C. by bubbling $H_2$ through a stainless steel $SiCl_4$ bubbler at −4° C. The total flow of $H_2$ and $SiCl_4$ was 109 sccm and the mole ratio of $H_2$ to $SiCl_4$ was 11.25:1. The gas and vapor leaving the bubbler was fed into the glass tube of a flow reactor containing the copper catalyst to form a silicon-containing copper catalyst comprising from 2-3% (w/w) Si. After 30 minutes the $SiCl_4$ flow was ceased and a hydrogen flow of 100 sccm was maintained while cooling to 300° C. over a period of 1 hour. When the reactor reached 300° C., all $H_2$ was purged from the reactor and catalyst with an argon flow of 50 sccm for 30 min. After 30 min, the argon flow was ceased, and MeCl was fed through the reactor at a flow rate of 5 sccm, 300° C., and atmospheric pressure. The reaction was periodically sampled and analyzed by GC/GC-MS as described above to determine the weight percent $Me_2SiCl_2$, based on the total mass leaving the reactor. Next, the MeCl feed was ceased, and the silicon-containing copper catalyst was contacted again with $H_2/SiCl_4$, to reform the silicon-containing copper catalyst, for 30 min at 750° C. The combined flow rate of $H_2$ and $SiCl_4$ was 109 sccm, and the mole ratio of $H_2$ to $SiCl_4$ was 11.25:1. After the silicon-containing copper catalyst was reformed, it was purged with argon, again, and MeCl was contacted with the reformed silicon-containing copper catalyst as described above. This cycle was repeated eight times. The results are shown in Table 2. This example demonstrates that diorganodihalosilane is produced by the method of the invention and that the selectivity and production of diorganodihalosilane improves with subsequent cycles of catalyst regeneration and reaction.

TABLE 2

Diorganodihalosilane production with increasing silicon-containing copper catalyst regeneration cycles.

| Time (min) | Me$_2$SiCl$_2$ (wt. %) | Me$_2$SiCl$_2$ Sel. | Time (min) | Me$_2$SiCl$_2$ (wt. %) | Me$_2$SiCl$_2$ Sel. | Time (min) | Me$_2$SiCl$_2$ (wt. %) | Me$_2$SiCl$_2$ Sel. |
|---|---|---|---|---|---|---|---|---|
| Cycle 1 | | | Cycle 2 | | | Cycle 3 | | |
| 1 | 0.00 | NA | 1 | 0.00 | NA | 1 | 0.00 | NA |
| 8 | 0.04 | 0.24 | 8 | 0.19 | 0.63 | 8 | 0.27 | 0.66 |
| 15 | 1.50 | 0.64 | 15 | 4.00 | 1.04 | 15 | 10.01 | 1.51 |
| 22 | 4.01 | 1.00 | 22 | 7.91 | 1.79 | 22 | 12.00 | 1.91 |
| 29 | 4.86 | 1.14 | 29 | 6.36 | 1.70 | 29 | 9.01 | 1.58 |
| 36 | 3.79 | 0.91 | 36 | 4.85 | 1.40 | 38 | 5.56 | 1.06 |
| 43 | 2.78 | 0.71 | 44 | 3.57 | 1.04 | 45 | 3.76 | 0.75 |
| 54 | 1.68 | 0.49 | 56 | 2.15 | 0.67 | 54 | 2.45 | 0.52 |
| 64 | 1.00 | 0.34 | 67 | 1.34 | 0.46 | 66 | 1.45 | 0.38 |
| 74 | 0.72 | 0.27 | 94 | 0.44 | 0.24 | | | |
| | | | 128 | 0.12 | 0.09 | | | |
| Cycle 4 | | | Cycle 5 | | | Cycle 6 | | |
| 1 | 0.00 | NA | 1 | 0.00 | NA | 1 | 0.00 | NA |
| 8 | 1.22 | 1.49 | 8 | 1.22 | 1.18 | 8 | 2.16 | 1.61 |
| 15 | 26.65 | 2.53 | 15 | 26.65 | 2.64 | 15 | 31.38 | 3.34 |
| 22 | 17.81 | 2.00 | 22 | 17.81 | 2.43 | 22 | 21.29 | 2.53 |
| 29 | 10.39 | 1.21 | 29 | 10.39 | 1.58 | 29 | 11.63 | 1.44 |
| 37 | 5.67 | 0.72 | 37 | 5.67 | 1.03 | 36 | 6.90 | 0.90 |
| 44 | 3.34 | 0.48 | 44 | 3.34 | 0.66 | 44 | 3.78 | 0.59 |
| 54 | 1.82 | 0.33 | 54 | 1.82 | 0.48 | 51 | 2.42 | 0.50 |
| 64 | 1.08 | 0.27 | 64 | 1.08 | 0.41 | 58 | 1.79 | 0.46 |
| 79 | 0.67 | 0.25 | 79 | 0.67 | 0.41 | 68 | 1.18 | 0.43 |
| 93 | 0.47 | 0.26 | 93 | 0.47 | 0.38 | 92 | 0.40 | 0.34 |
| 104 | 0.32 | 0.26 | 104 | 0.32 | 0.34 | 104 | 0.20 | 0.26 |
| Cycle 7 | | | Cycle 8 | | | | | |
| 1 | 0.03 | No other | 1 | 0.00 | NA | | | |
| 8 | 2.82 | 1.68 | 8 | 2.16 | 1.42 | | | |
| 15 | 18.69 | 2.79 | 15 | 31.38 | 3.08 | | | |
| 23 | 20.17 | 2.53 | 22 | 21.29 | 3.30 | | | |
| 30 | 12.21 | 1.59 | 29 | 11.63 | 2.54 | | | |
| 37 | 6.71 | 0.93 | 36 | 6.90 | 1.75 | | | |
| 46 | 3.19 | 0.53 | 44 | 3.78 | 1.19 | | | |
| 56 | 1.88 | 0.44 | 51 | 2.42 | 0.85 | | | |
| 77 | 0.82 | 0.42 | 58 | 1.79 | 0.65 | | | |
| 104 | 0.20 | 0.24 | 68 | 1.18 | 0.49 | | | |
| | | | 92 | 0.40 | 0.43 | | | |
| | | | 104 | 0.20 | 0.40 | | | |

Example 2

Copper catalysts as listed below Table 3 were prepared following a procedure similar to that described before example 1 above. The catalysts were treated for 30 minutes with hydrogen and silicon tetrachloride as described in example 1 and in a mole ratio of hydrogen to silicon tetrachloride and at the temperature indicated in Table 2. As described in example 1, after treatment with the hydrogen and silicon tetrachloride then just hydrogen, the reactor and catalyst were purged with argon. After the argon purge, methyl chloride was introduced into the reactor at the flow rate of 5 sccm, 300° C., and atmospheric pressure. The reaction was sampled at various times to evaluate the dimethyldichlorosilane production by GC/GC-MS. The production of dimethyldichlorosilane and the reaction time are listed in Table 3. This example demonstrates the other elements that may be used in the copper catalyst to produce diorganodihalosilanes.

TABLE 3

Various copper catalysts evaluated, conditions and dimethyldichlorosilane production.

| Catalyst | Catalyst Mass (g) | SiCl$_4$ Flow (sccm) | H$_2$:SiCl$_4$ Ratio | Temp. (° C.) | Total reaction time (min) | Me$_2$SiCl$_2$ (mg) | Me$_2$SiCl$_2$ Sel. |
|---|---|---|---|---|---|---|---|
| 1 | 0.86 | 40.1 | 2.49:1 | 650 | 107 | 32.6 | 1.16 |
| 2 | 0.84 | 40.1 | 2.49:1 | 650 | 85 | 14.3 | 0.58 |
| 3 | 0.67 | 40.1 | 2.49:1 | 650 | 122 | 14.4 | 0.53 |
| 4 | 0.70 | 8.9 | 11.25:1 | 750 | 187 | 34.6 | 0.89 |
| 5 | 0.77 | 8.9 | 11.25:1 | 850 | 104 | 87.0 | 1.47 |

TABLE 3-continued

Various copper catalysts evaluated, conditions and dimethyldichlorosilane production.

| Catalyst | Catalyst Mass (g) | SiCl$_4$ Flow (sccm) | H$_2$:SiCl$_4$ Ratio | Temp. (° C.) | Total reaction time (min) | Me$_2$SiCl$_2$ (mg) | Me$_2$SiCl$_2$ Sel. |
|---|---|---|---|---|---|---|---|
| 6 | 0.80 | 8.9 | 11.25:1 | 750 | 104 | 59.0 | 1.17 |
| 7 | 0.80 | 40.1 | 2.49 | 650 | 119 | 4.0 | 0.20 |

Key to Catalysts in Table 3:
1. 23% Cu on activated carbon
2. 30.7% Cu and 1.0% Ca on activated carbon
3. 19.8% Cu and 0.14% Sn on activated carbon
4. 19.1% Cu and 0.87% Au on activated carbon
5. 22.3% Cu, 0.71% Au and 0.24% Mg on activated carbon
6. 20% Cu, 0.7%, Au, and 3% S on activated carbon
7. 22.9% Cu, 1.4% Cs on activated carbon Example 3

In a flow reactor, 0.69 g of an activated carbon supported catalyst comprising 20.9% (w/w) Cu (as CuCl$_2$) and 0.63% (w/w) Au (as AuCl$_3$) were loaded into a glass tube. Hydrogen was then introduced at a 100 sccm flow rate and 600° C. for two hours. The reaction tube was then cooled to room temperature under H$_2$, transferred via an air-tight stainless steel system to an environmentally controlled Ar glove box, weighed, and then placed back into the reactor setup. Hydrogen was then fed at a flow rate of 100 sccm through a bubbler containing SiCl$_4$ at temperature from 0 to 5° C. and then to the flow reactor to contact the copper catalyst at 750° C. for 30 minutes. After 30 minutes, the flow of hydrogen through the SiCl$_4$ bubbler was stopped and the catalyst reduced under hydrogen at 600° C. for 1 hour. The reaction tube was then cooled to room temperature under H$_2$, weighed as above, and returned to the reactor setup. The reactor was then heated to 300° C. while 50 sccm Ar was flowed over the catalyst. Once 300° C. was reached, Ar flow was ceased, and a 5 sccm flow of MeCl to the reaction tube was started. Samples were taken from the reaction stream and injected into a GC-TCD for analysis. The reaction tube was then again cooled, weighed, and placed back into the reactor setup as described above. This process was repeated for 10 cycles using the same parameters. Based upon the mass of Si added, approximately 3% (w/w), based on the weight of the silicon, copper, gold, and support, of the catalyst was composed of Si after treatment of the catalyst each time with H$_2$ and SiCl$_4$ at 750° C. During the tenth cycle, the process produced Me$_2$SiCl$_2$ at a selectivity of 1.24. This example demonstrates that the catalyst can be regenerated and reacted to produce diorganodihalosilanes and an amount of silicon in the silicon-containing catalyst after treatment with the silicon tetrahalide and hydrogen of about 3%.

That which is claimed is:

1. A method of preparing a diorganodihalosilane, the method comprising the following separate and consecutive steps:
   (i) contacting a copper catalyst with a mixture comprising hydrogen gas and a silicon tetrahalide at a temperature of from 500 to 1400° C. to form a silicon-containing copper catalyst comprising from 1 to 5% (w/w) of silicon, wherein the copper catalyst is selected from copper and a mixture comprising copper and at least one element selected from gold, magnesium, calcium, cesium, tin, and sulfur; and
   (ii) contacting the silicon-containing copper catalyst with an organohalide at a temperature of from 100 to 600° C. to form at least one diorganodihalosilane.

2. The method according to claim 1, further comprising (iii) contacting the silicon-containing copper catalyst contacted with the organohalide in step (ii) with the mixture comprising hydrogen gas and a silicon tetrahalide at a temperature of from 500 to 1400° C. to reform the silicon containing copper catalyst comprising at least 0.1% (w/w) silicon; and (iv) contacting the reformed silicon-containing copper catalyst with the organohalide at a temperature of from 100 to 600° C. to form at least one diorganodihalosilane.

3. The method according to claim 2, further comprising repeating steps (iii) and (iv) at least 1 time.

4. The method according to claim 2, further comprising purging prior to the contacting of the reformed silicon-containing copper catalyst with the organohalide in step (iv).

5. The method according to claim 4, wherein the purging is conducted with argon or silicon tetrachloride.

6. The method according to claim 1, further comprising purging prior to contacting the silicon-containing copper catalyst with the organohalide in step (ii).

7. The method according to claim 6, wherein the purging is conducted with argon or silicon tetrachloride.

8. The method according claim 1, wherein the copper catalyst is supported.

9. A method of preparing a diorganodihalosilane, the method comprising the following separate and consecutive steps:
   (i) contacting a copper catalyst with a mixture comprising hydrogen gas and a silicon tetrahalide at a temperature of from 500 to 1400° C. to form a silicon-containing copper catalyst comprising, from 1 to 5% (w/w) of silicon wherein the copper catalyst comprises from 0.1 to 35% (w/w) of a mixture and the mixture comprises copper, gold and magnesium, and
   (ii) contacting the silicon-containing copper catalyst with an organohalide at a temperature of from 100 to 600° C. to form at least one diorganodihalosilane.

10. The method according to claim 8, wherein the support is activated carbon.

11. The method according to claim 1, wherein mole ratio of hydrogen to silicon tetrahalide is from 20:1 to 5:1.

12. The method according to claim 1, wherein the silicon tetrahalide is silicon tetrachloride.

13. The method according to claim 1, wherein the organohalide has formula Rx, where R is C$_1$-C$_{10}$ alkyl or C$_4$-C$_{10}$ cycloalkyl and X is fluoro, chloro, bromo, or iodo.

14. The method of claim 13, wherein R is methyl and X is chloro.

15. The method according to claim 1, wherein the contacting in (ii) is in the absence of hydrogen.

16. The method according to claim 1, wherein the diorganodihalosilane has the formula $R_2SiX_2$, where R is $C_1$-$C_{10}$ alkyl or $C_4$-$C_{10}$ cycloalkyl and X is fluoro, chloro, bromo, or iodo.

17. The method according to claim 16, wherein R is methyl and X is chloro.

18. The method according to claim 1, further comprising recovering the diorganodihalosilane.

19. The method according to claim 1, wherein the residence time of the hydrogen and silicon tetrahalide is from 0.5 to 10 s and the residence time of the organohalide is from 1 to 10 s.

\* \* \* \* \*